(12) United States Patent
Sooy

(10) Patent No.: US 7,889,980 B2
(45) Date of Patent: Feb. 15, 2011

(54) GRAPHICAL REPRESENTATION OF ENCLOSED INSPECTION AREA

(75) Inventor: Josh Sooy, Elyria, OH (US)

(73) Assignee: Emerson Electric Co., St. Louis, MO (US)

( * ) Notice: Subject to any disclaimer, the term of this patent is extended or adjusted under 35 U.S.C. 154(b) by 137 days.

(21) Appl. No.: 12/275,693

(22) Filed: Nov. 21, 2008

(65) Prior Publication Data

US 2010/0125959 A1 May 27, 2010

(51) Int. Cl.
G03B 37/00 (2006.01)
H04N 7/18 (2006.01)
B08B 9/02 (2006.01)

(52) U.S. Cl. .............................. 396/19; 348/84; 348/85; 15/104.33

(58) Field of Classification Search .................... 396/19; 348/82, 84, 85; 340/670; 116/113; 15/104.33
See application file for complete search history.

(56) References Cited

U.S. PATENT DOCUMENTS

| | | | |
|---|---|---|---|
| 3,007,186 A * | 11/1961 | Olsson | .................... 15/104.33 |
| 5,742,517 A | 4/1998 | Van Den Bosch | |
| 6,175,380 B1 | 1/2001 | Van Den Bosch | |
| 6,545,704 B1 * | 4/2003 | Olsson et al. | ................. 348/84 |
| 7,010,759 B2 * | 3/2006 | Janu | ........................... 715/848 |
| 2006/0290779 A1 * | 12/2006 | Reverte et al. | ................ 348/84 |
| 2008/0148503 A1 | 6/2008 | Babb et al. | |

* cited by examiner

Primary Examiner—Christopher E Mahoney
Assistant Examiner—Noam Reisner
(74) Attorney, Agent, or Firm—Harness, Dickey & Pierce, P.L.C.

(57) ABSTRACT

An apparatus for generating a visual representation may include an elongated flexible member adapted to be removably inserted into an enclosure; a dispensing mechanism operable to selectively dispense and retract the elongated flexible member; a counter configured to determine an amount of the elongated flexible member dispensed by the dispensing mechanism; a controller configured to receive the amount of the elongated flexible member dispensed from the counter and determine a rate at which the elongated flexible member is dispensed; and a display in data communication with the controller. The controller causes the rate at which the flexible member is dispensed to be displayed in relation to a visual representation of the enclosure on the display.

24 Claims, 7 Drawing Sheets

GRAPHICAL REPRESENTATION OF ENCLOSED INSPECTION AREA

FIELD

The present disclosure relates to a visual representation of an enclosure and more particularly to a graphical representation of an enclosed inspection area.

BACKGROUND

Enclosed areas such as pipes, drains, ducts, other passages and enclosures are often difficult to service and inspect due to the limited accessibility of these areas. Probes or plumbing snakes are often employed to probe for blockages, impediments or damage to the enclosure, for example. Plumbing snakes can be fitted with an auger, drill or other tool to cut away at least a portion of the impediments or blockages to facilitate unrestricted flow through the enclosure.

Root systems of mature trees can pose a recurring problem for underground plumbing of many homes and other buildings. Roots can grow through pipes, impeding or blocking flow therethrough. As described above, a plumbing snake having a cutting tool can cut away the roots, however, over a period of time, the roots may grow back and restrict the flow through the pipes. Each time the pipe is cleared, the service technician or homeowner often has to rediscover the precise number and locations of the impediments, in order to be confident that all problem areas have been addressed. This can increase the cost and time required to complete a service job. Further, service technicians and homeowners are often unable to efficiently and comprehensively inspect the enclosure to verify the completeness and thoroughness of the job.

This section provides background information related to the present disclosure which is not necessarily prior art.

SUMMARY

This section provides a general summary of the disclosure, and is not a comprehensive disclosure of its full scope or all of its features.

In one form, the present disclosure provides An apparatus for generating a visual representation may include an elongated flexible member adapted to be removably inserted into an enclosure; a dispensing mechanism operable to selectively dispense and retract the elongated flexible member; a counter configured to determine an amount of the elongated flexible member dispensed by the dispensing mechanism; a controller configured to receive the amount of the elongated flexible member dispensed from the counter and determine a rate at which the elongated flexible member is dispensed; and a display in data communication with the controller. The controller causes the rate at which the flexible member is dispensed to be displayed in relation to a visual representation of the enclosure on the display.

In another form, the present disclosure provides an apparatus which may include a support; a drum rotatably coupled to the support, the drum including a housing portion defining an opening therethrough; a cable coiled around the drum and adapted to selectively dispense therefrom through the opening and into an enclosure; a cable follower rotatable relative to the drum and configured to guide the cable through the opening; a first sensor fixed relative to a portion of the drum; a second sensor fixed relative to a portion of the cable follower, the first and second sensors sensing relative movement therebetween and generating a signal indicative of the relative movement; and a controller adapted to receive the signal and determine an amount of cable dispensed and a rate at which the cable is dispensed based on the signal. The controller may be operable to generate a visual representation including indicia of the rate at which the cable is dispensed relative to a segment of the enclosure and indicia of a change in the rate relative to the segment of the enclosure.

In yet another form, the present disclosure provides an apparatus which may include a flexible member adapted to be removably fed into an enclosure through an opening therein; a camera disposed on a distal end of the flexible member and adapted to capture at least one image frame within the enclosure; a counting device configured to determine a distance that the distal end has been fed into the enclosure; and a controller in communication with the camera and the counting device. The controller may be adapted to generate a visual representation of at least a segment of the enclosure. The visual representation may include indicia of distances from the opening in the enclosure over which the distal end has been fed. The at least one image frame may be associated with at least one of the indicia of distances and may be selectively viewable in the visual representation.

Further areas of applicability will become apparent from the description provided herein. The description and specific examples in this summary are intended for purposes of illustration only and are not intended to limit the scope of the present disclosure.

DRAWINGS

Figure 1:
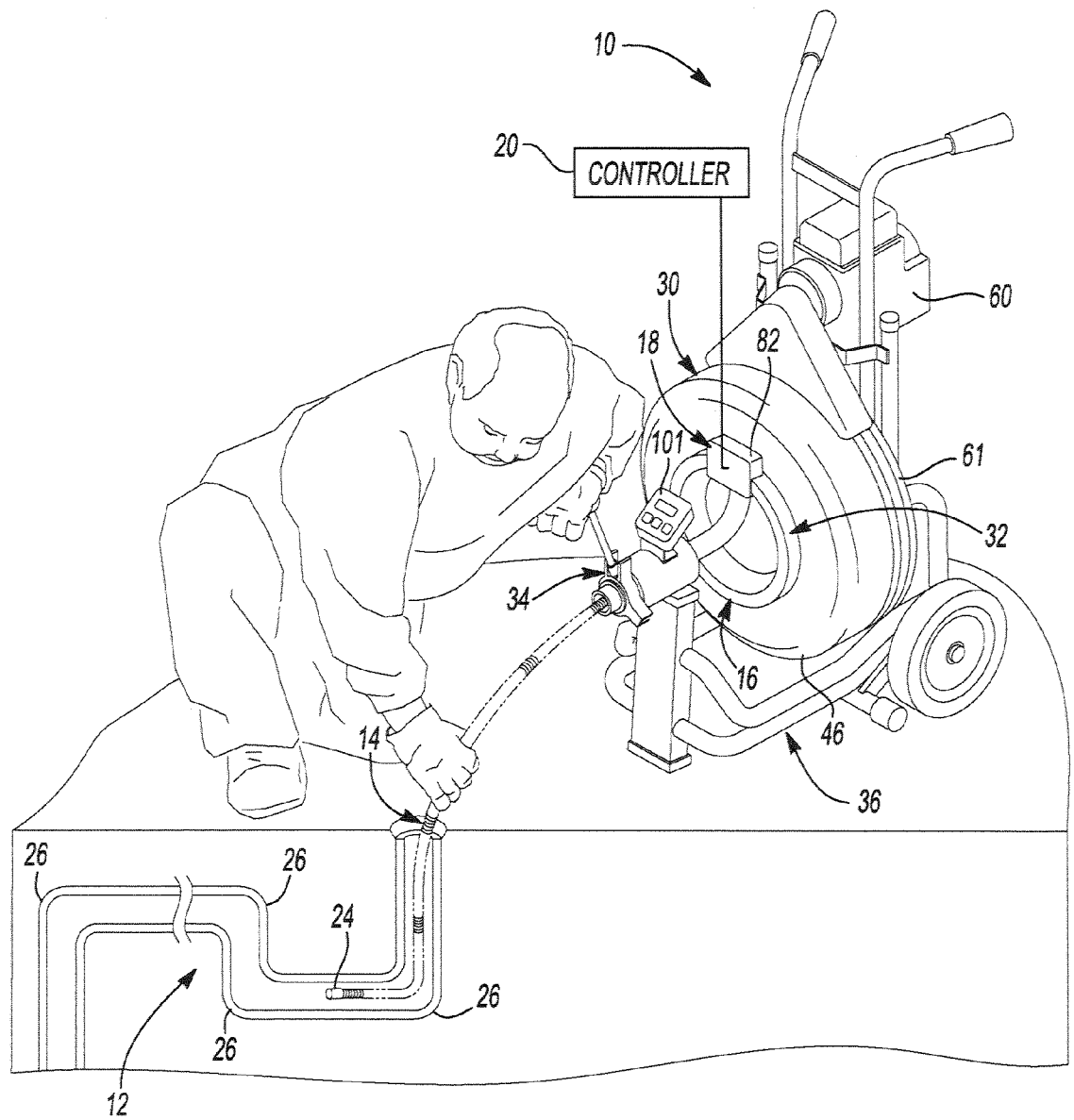
FIG. 1 is a perspective view of a probing apparatus including an elongate flexible member being fed into an enclosure according to the principles of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Example embodiments will now be described more fully with reference to the accompanying drawings.

With reference to FIGS. 1-10, an exemplary probing apparatus 10 is provided and may be operable to probe, inspect and/or clear foreign matter and blockages from an enclosure 12. As will be subsequently described, the probing apparatus 10 can be configured to generate a visual representation of at least a portion of the enclosure 12 and provide other information to aid in the diagnosis, service and/or inspection of the enclosure 12. The probing apparatus 10 may include a flexible member 14 that can be removably inserted into the enclosure 12, a dispensing mechanism 16 configured to selectively dispense and retract the flexible member 14, a cable counter 18 that can determine an amount of the flexible member 14 which has been inserted into the enclosure 12, and a controller 20 adapted to generate the visual representation of the enclosure 12. While the enclosure 12 is illustrated in the figures as a drain or pipe, it will be appreciated that the enclosure 12 could be any enclosed area such as, for example, a heating, ventilation and air conditioning (HVAC) duct, a port or passage in an engine, enclosed framework of a building, or any other conduit, passage or hard to reach area.

The flexible member 14 includes a proximal end 22 coupled to the dispensing mechanism 16 and a distal end 24 that can be removably inserted into the enclosure 12. The flexible member 14 may be an elongated cable, for example, with sufficient flexibility to be resiliently bent or flexed to navigate through one or more turns or bends 26 in the enclosure 12. The flexible member 14 may be sufficiently stiff to facilitate transmission of force therethrough to the distal end 24. The flexible member 14 can be a plumbers' snake or other similar device known in the art, and can be formed from metal, plastic, rubber or a composite material, for example, or any other material suited for a given application.

Figure 2:
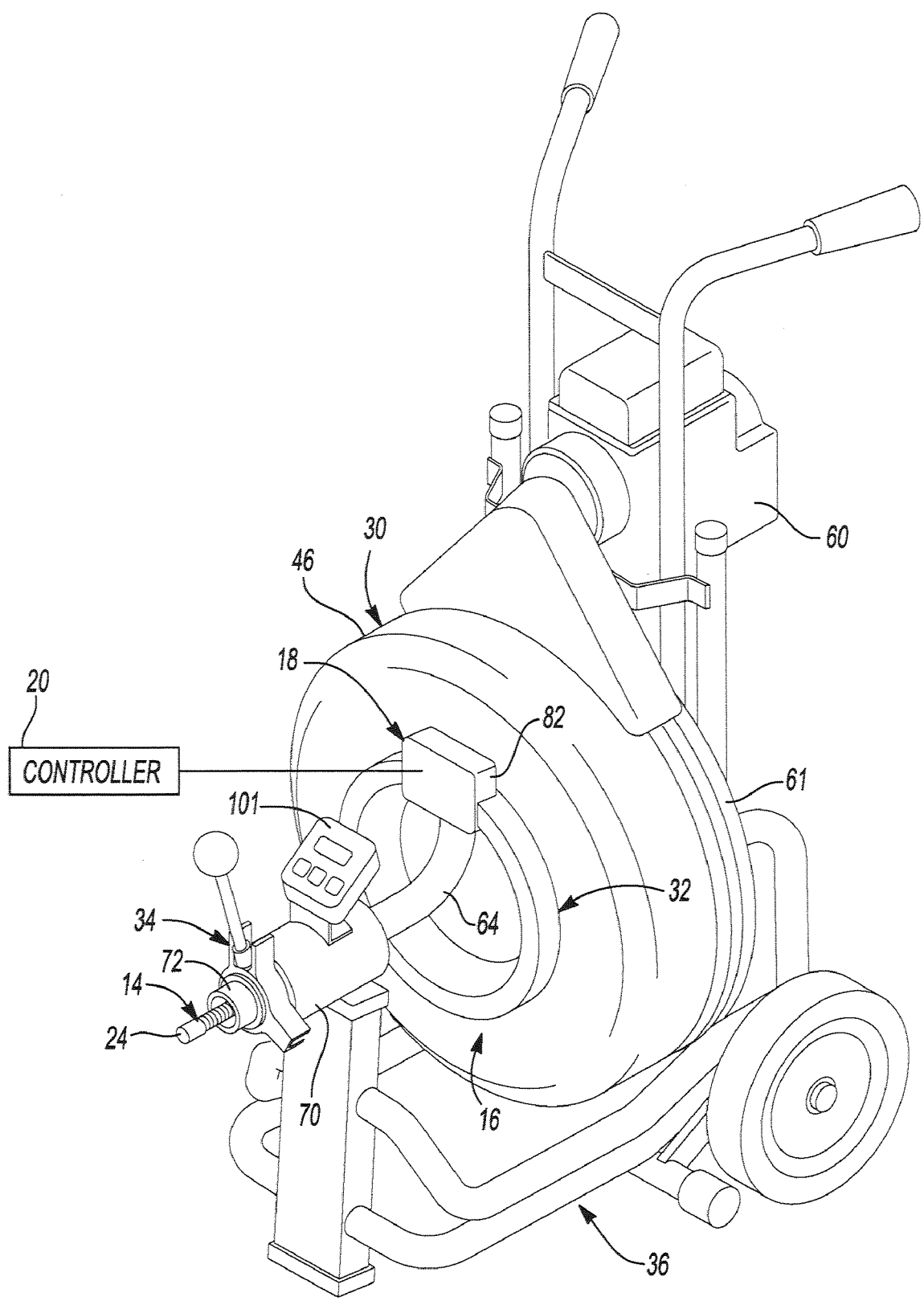
FIG. 2 is a perspective view of the probing apparatus of FIG. 1.
Figure 3:
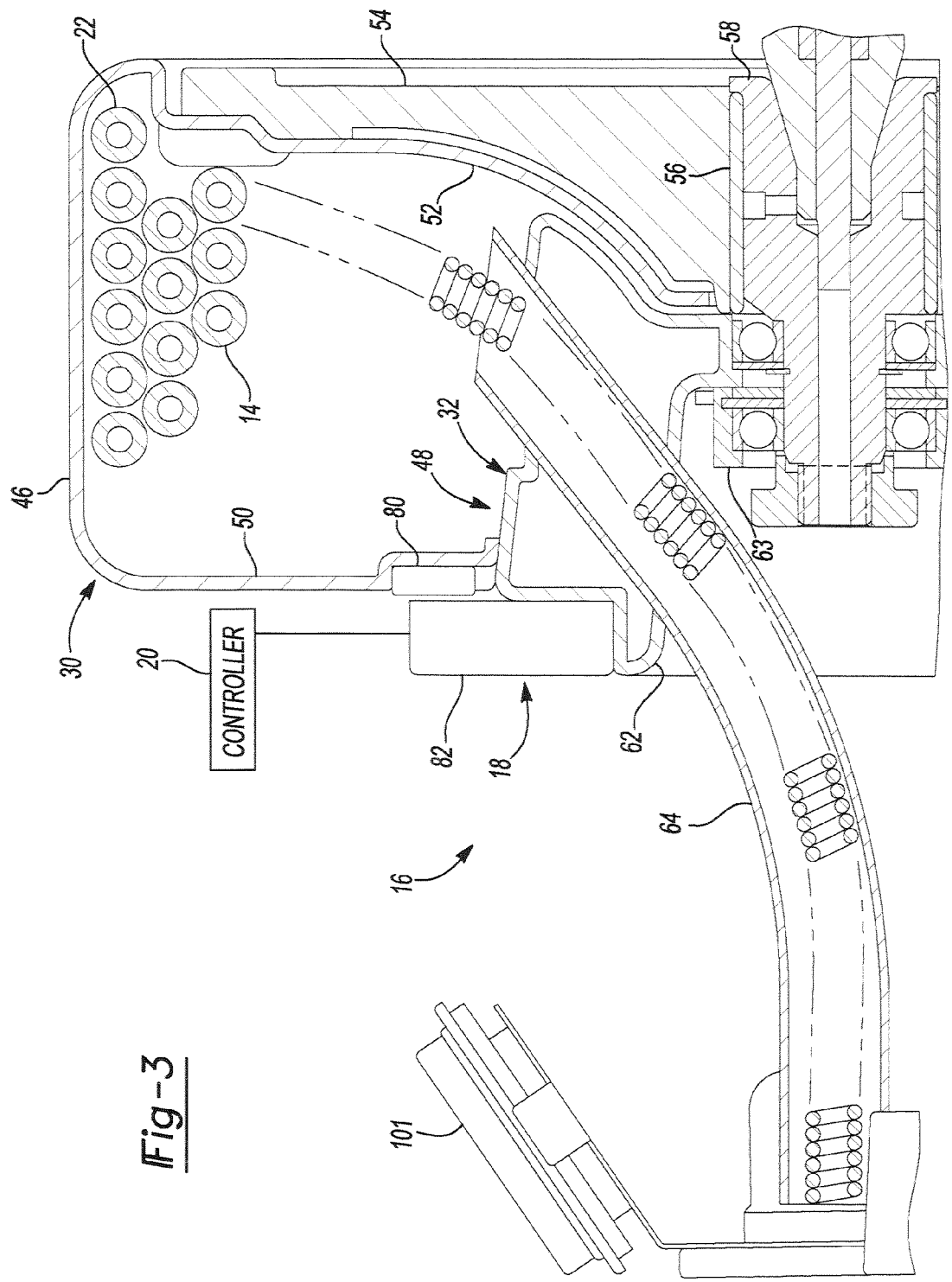
FIG. 3 is a partial cross-sectional view of a dispensing mechanism and cable counter device according to the principles of the present disclosure.

Referring now to FIGS. 1-3, the dispensing mechanism 16 may include a drum assembly 30, a cable follower 32 and a feed control mechanism 34. The drum assembly 30 may include a drum housing 46 having an opening 48 in a front wall 50 thereof and having its rear wall 52 contoured to engage a hub member 54. A hollow drum shaft 56 supported by an elongate member 58 may be secured to a frame 36 and may be rotatable about an axis defined by the elongate member 58. The flexible member 14 can be coiled within the drum housing 46, as shown in FIG. 3. An electric drive motor 60 may drive a belt 61 which in turn may drivingly engage the outer periphery of the drum housing 46 to rotate the drum housing 46 about the longitudinal axis of the elongate member 58. Rotation of the drum housing 46 causes the flexible member 14 to rotate about its longitudinal axis, thereby rotating a cutting tool 59 (FIG. 4) which may be disposed on the distal end 24 of the flexible member 14.

The cable follower 32 may include an inner drum 62 and a guide tube 64. The inner drum 62 may be coupled to the outer end of the elongate member 58 by a mounting bracket 63 or the like using suitable bearings and fasteners. The cable follower 32 guides the flexible member 14 into and out of the opening 48 of the drum housing 46. While the cable follower 32 is illustrated and described herein as being a part of the drum assembly 30, the guide tube 64 could be supported adjacent its axially outer end for rotation, in which case it would be free of a mounted interconnection with the drum assembly 30. Further, while the drum housing 46 and hub member 54 are described above as being separate components, the drum housing 46 could be constructed so as to provide an integrally formed hub portion.

The feed control mechanism 34 may include a feed housing 70 having an opening 72 therethrough generally coaxial with the drum housing 46 and the elongate member 58. The feed control mechanism 34 may further include a plurality of cam members and other movable members which may be adapted to selectively engage the flexible member 14 as it rotates to selectively dispense the flexible member 14 through the guide tube 64 and the opening 72 and selectively cause the flexible member 14 to retract into its coiled configuration within the drum housing 46.

The cable follower 32 may be rotatable in a first direction relative to the drum housing 46 to unwind the flexible member 14 from the drum housing 46. Conversely, the cable follower 32 may be rotatable in a second direction relative to the drum housing 46 to wind the flexible member 14 back into the coiled configuration within the drum housing 46. The cable follower 32 may rotate 360 degrees relative to the drum housing 46 to dispense or retract a single wrap or turn of the flexible member 14.

The cable counter 18 may include a first sensor 80 fixed relative to the drum housing 46, and a second sensor 82 fixed relative to the cable follower 32. The first and second sensors 80, 82 are adapted to sense an amount and direction of relative rotational motion between the drum housing 46 and the cable follower 32. Either or both of the sensors 80, 82 may be adapted to generate a signal indicative of the amount and direction of relative rotational motion and communicate the signal to the controller 20. The signal generated by the first and/or second sensors 80, 82 and received by the controller 20 can be a radio frequency signal or any other suitable wireless signal. Accordingly, it will be appreciated that the controller 20 could be disposed remotely from the probing apparatus 10. It will also be appreciated that the controller 20 can be mounted to the probing apparatus 10 in any suitable location. As such, the first or second sensor 80, 82 could be wired to the controller 20 for communication therebetween via the wired connection.

The first and second sensors 80, 82 may include a set of magnets and Hall Effect sensors, respectively, which may cooperate to sense pulses or switch closures as the magnets rotate adjacent the Hall Effect sensors. In this manner, the cable counter 18 and controller 20 may cooperate to determine an amount of the flexible member 14 that has been dispensed from the dispensing mechanism 16. It will be appreciated that the first and second sensors 80, 82 could be any suitable type of sensors operable to detect relative motion therebetween.

Further details of the exemplary dispensing mechanism 16 and exemplary cable counter 18 are provided in U.S. patent application Ser. No. 12/188,433, the disclosure of which is hereby incorporated by reference as if fully set forth herein in its entirety. It will be appreciated that the dispensing mechanism 16 and cable counter 18 could be otherwise suitably configured. For example, the dispensing mechanism 16 could be any suitable mechanism operable to dispense a cable or other elongated flexible member. Likewise, the cable counter 18 could be any suitable device operable to determine an amount of cable or flexible member that has been dispensed from the dispensing mechanism and communicate that amount to an intelligent device, which may be a computer, a controller, a processor or the like.

By means of a further example, the dispensing mechanism 16 could be of the type disclosed in U.S. Publication No. 2008/0148503, the disclosure of which is hereby incorporated by reference as if fully set forth herein in its entirety. As described more fully therein and partially illustrated in FIG. 4 of the present disclosure, the probing apparatus 10 could be a hand-held probing apparatus 10' having a power drill 90, or a similar device, adapted to selectively rotate a drum assembly 30' in first and second directions. The flexible member 14 may be coiled within the drum assembly 30' and can be dispensed through a guide tube 64' in response to the drum assembly 30' being rotated in the first direction. Similarly, the flexible member 14 can be retracted back into the drum assembly 30' to be stored in a coiled configuration in response to the drum assembly 30' being rotated in the second direction. A collar 92 may be disposed around a nose portion 94 of the drum assembly 30' and may be rotatable relative thereto, such that the collar 92 can remain fixed relative to the power drill 90 if an operator grasps the collar 92 for additional support during operation of the hand-held probing apparatus 10'. The particular embodiment illustrated in FIG. 4 includes the optional cutting tool 59 disposed on the distal end 24 of the flexible member 14, which may be operable to remove debris that may be clogging the enclosure 12.

Figure 4:
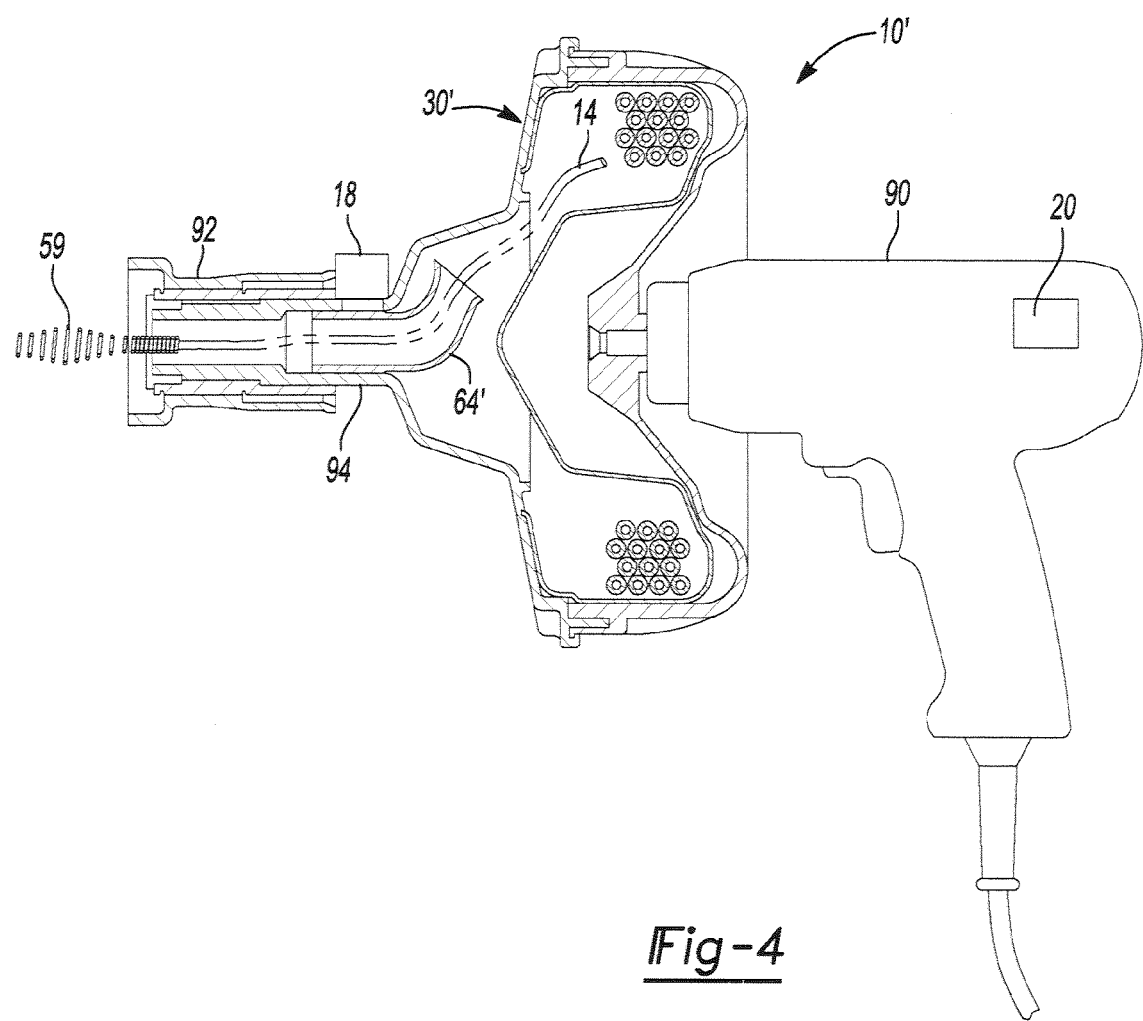
FIG. 4 is a cross-sectional view of another embodiment of a probing apparatus.

The cable counter 18 described herein (or any other suitably configured cable counting device) can be incorporated into the hand-held probing apparatus 10' shown in FIG. 4. For example, one of the first and second sensors 80, 82 could be disposed on the drum assembly 30', and the other of the first and second sensors 80, 82 could be disposed on the collar 92 or any other location that is rotationally fixed relative to the drum assembly 30'. In this manner the first and second sensors 80, 82 can cooperate to sense relative rotational motion therebetween and communicate a signal indicative of the direction and amount of relative rotational motion to the controller 20, which could be disposed within the power drill 90, for example.

It will be appreciated that the dispensing mechanism 16 can be manually powered. That is, a dispensing mechanism that does not have an electric motor or other source of rotary motive power is equally applicable to the principles of the present disclosure. Further examples of probing apparatuses having suitable dispensing mechanisms are described in U.S. Pat. Nos. 2,468,490; 2,730,740; 3,007,186; 3,394,422; 3,095,592; 3,134,119; 3,246,354; 4,364,139; 4,580,306; 5,031,276; and 6,009,588, the disclosures of which are all hereby incorporated by reference as if fully set forth herein in their entireties.

Figure 5:
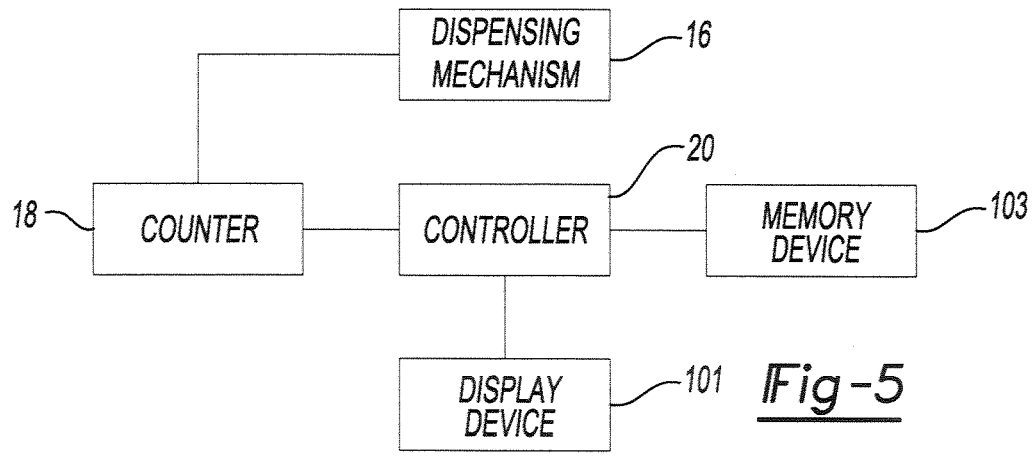
FIG. 5 is a block diagram of the probing apparatus of FIG. 2 and/or FIG. 4.

Referring now to FIGS. 1-8, the probing apparatus 10, 10' may further include a display device 101 and a memory device 103, both of which may be in communication with the controller 20, as shown in FIG. 5. The display device 101 can be an LCD screen, a portable monitor, a laptop computer, an operator interface module or any other suitable device capable of displaying visual media. The display device 101 may be mounted to the probing apparatus 10, 10' (FIGS. 1-3) or it may be remotely disposed and adapted to communicate with the controller 20 wirelessly.

Figure 6:
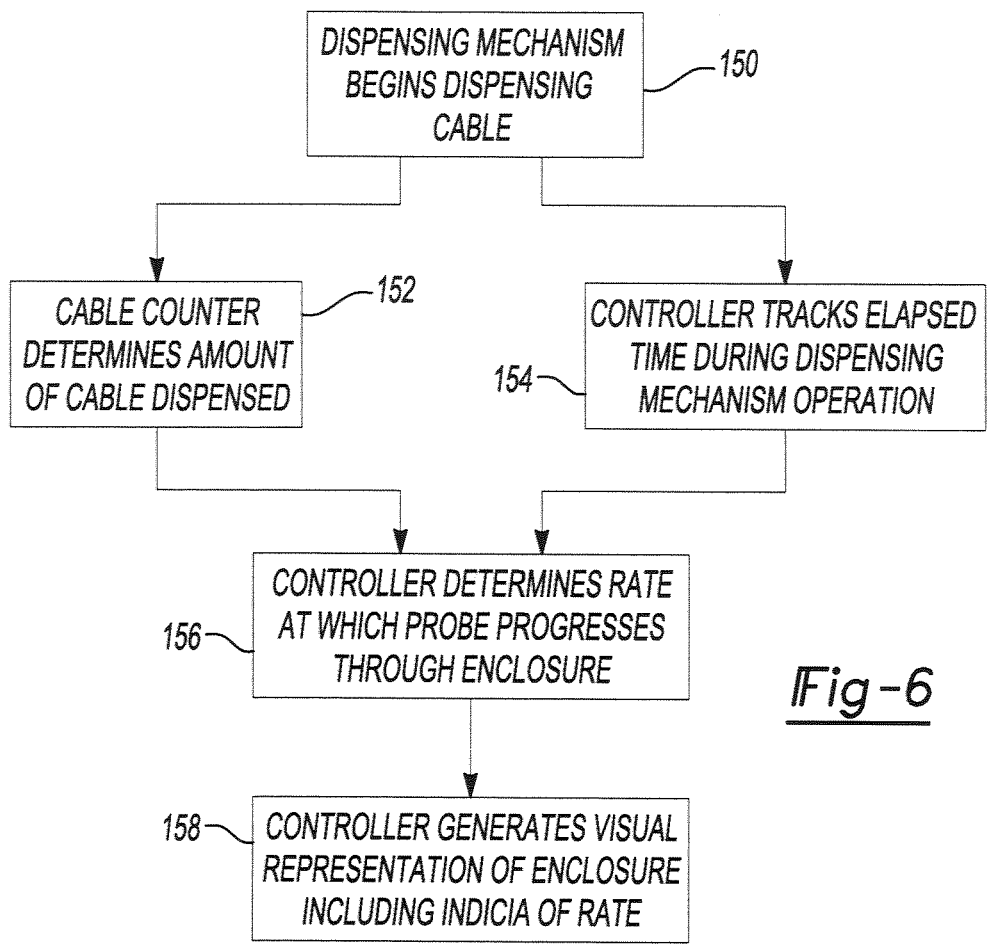
FIG. 6 is a flowchart illustrating the operation of the enclosure visualization system according to the principles of the present disclosure.

The controller 20 may be configured to determine a rate at which the flexible member 14 progresses into the enclosure 12 and generate a visual representation 100 (FIG. 8) of the enclosure 12 including indicia of the rate, as will be subsequently described. As shown in FIG. 6, at step 150, the dispensing mechanism 16 begins dispensing the flexible member 14 into the enclosure 12. At step 152, the controller 20 may continuously or intermittently receive the signal from the sensors 80, 82 indicative of the amount of the flexible member 14 that has been dispensed, as described above. At step 154, the controller 20 may simultaneously track an elapsed time since the dispensing mechanism 16 began dispensing the flexible member 14. Having received the amount of the flexible member 14 that has been dispensed, and the amount of time over which the flexible member 14 has been dispensed, the controller 20 can determine the rate at which the flexible member 14 is progressing through the enclosure 12 at step 156. The controller 20 may incrementally communicate the amount of the flexible member 14 that has been dispensed and the rate at which it is dispensed to the memory device 103 to be stored therein. For example, the memory device 103 may store the amount and rate in predetermined time increments or predetermined length increments. At step 158, the controller 20 may generate a signal which can cause the visual representation 100 of the enclosure 12 to be displayed. The controller 20 may communicate this signal to the memory device 103 and/or the display device 101 to display the visual representation 100 thereon. The memory device 103 can electronically store the visual representation 100 such that the operator or technician can retrieve and view the visual representation 100 at a future point in time.

Figure 8:
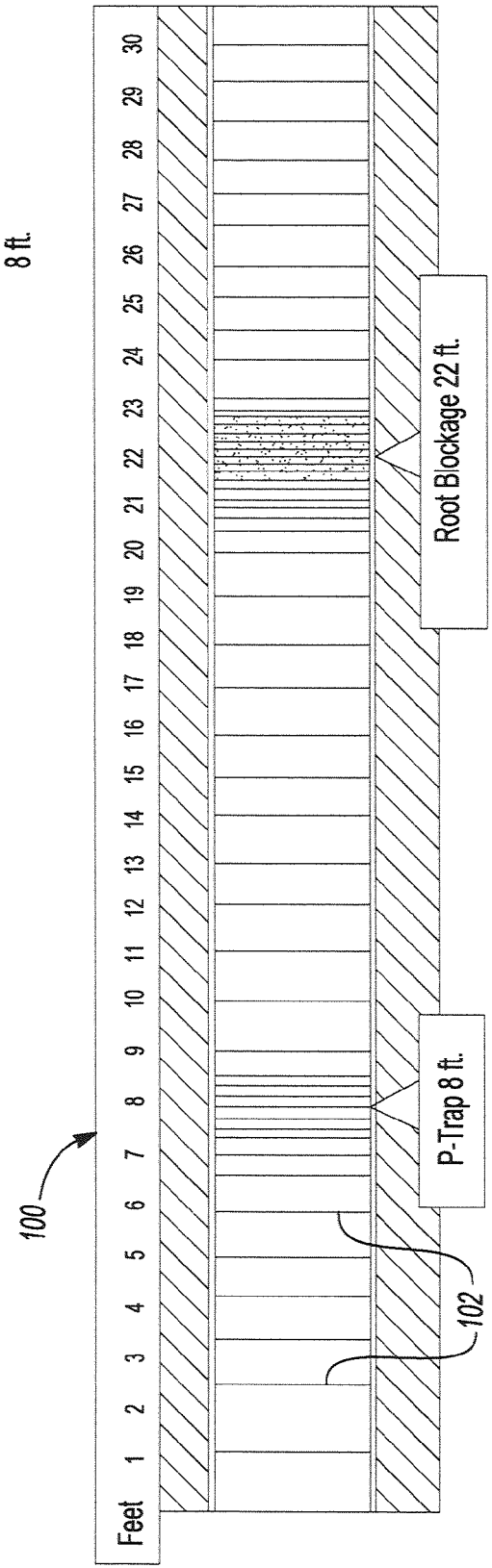
FIG. 8 is a visual representation of the enclosure of FIG. 7 according to the principles of the present disclosure.

The visual representation 100 may include indicia of distance from the opening of the enclosure 12. For example, as shown in FIG. 8, the indicia of distance from the opening can include a linear scale of the distance in feet spanning a schematic illustration of the enclosure 12. It will be appreciated that the visual representation 100 could indicate the distance in any unit of measurement including inches, yards, centimeters, meters, or any other suitable unit. It will also be appreciated that the indicia of distance could additionally or alternatively include any suitable indicator of distance, and is not limited to a linear, numeric scale.

The visual representation 100 may also include indicia of the rate at which the flexible member 14 is progressing through the enclosure 12. As described above, the cable counter 18 determines the amount of the flexible member 14 that has been dispensed by the dispensing mechanism 16 and communicates that amount to the controller 20 such that the location of the distal end 24 of the flexible member 14 can be determined. Once every predetermined time interval, the location of the distal end 24 of the flexible member 14 can be mapped and represented as a line 102. In this manner, the spacing of the lines 102 indicates the rate at which the flexible member 14 is progressing through the enclosure 12 relative to the distance from the opening of the enclosure 12. For example, if adjacent lines 102 are spaced relatively far apart from each other proximate a first distance from the opening, this indicates that the flexible member 14 was progressing through the enclosure 12 at a relatively high rate proximate the first distance. Conversely, if adjacent lines 102 are spaced relatively close together proximate a second distance, this indicates a relatively slower progression through the enclosure 12 proximate the second distance.

Figure 7:
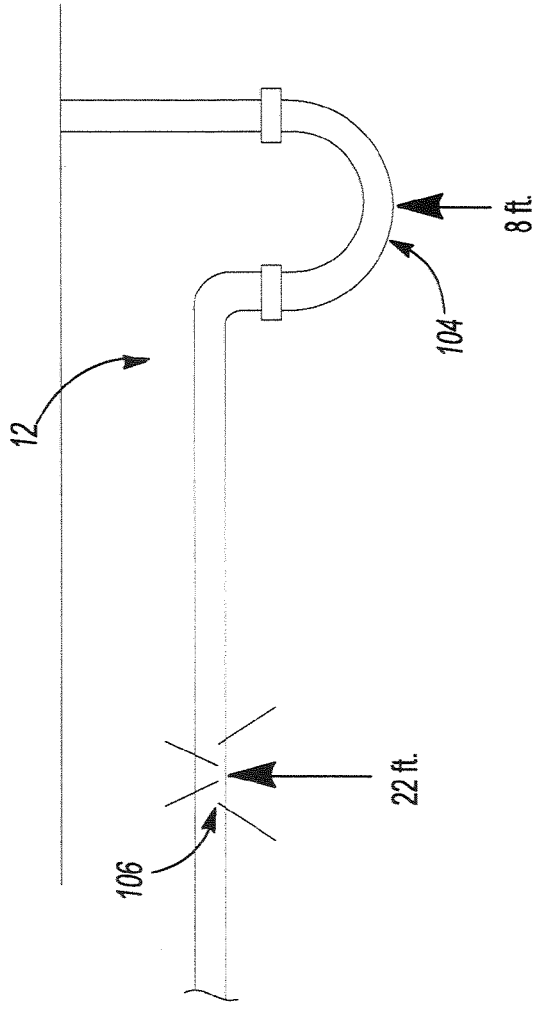
FIG. 7 is a cross-sectional view of an enclosure having a flow-restricting blockage.

To further illustrate the above concept, FIG. 7 shows an exemplary enclosure 12 illustrated as a drain pipe, and FIG. 8 is an example of the visual representation 100 which may represent the enclosure 12 of FIG. 7. The enclosure 12 illustrated includes a bend 104 and a blockage 106. The bend 104 could be a P-trap, for example, or any other bend or curve in the enclosure 12. The blockage 106 can be one or more tree roots that have grown through the enclosure or any other foreign matter or debris restricting flow through the enclosure 12. In the particular example illustrated, the bend 104 is located about seven to nine feet from the opening, and the blockage is located about twenty to twenty three feet from the opening. The rate at which the flexible member 14 can progress through the enclosure 12 during operation of the probing apparatus 10 or 10' may decrease as the distal end 24 of the flexible member 14 encounters the bend 104 and/or the blockage 106. FIG. 8 illustrates this situation, as adjacent lines 102 are spaced closer together between approximately the seven-foot position and the nine-foot position on the distance scale, which corresponds with the bend 104. After about the nine-foot position, the flexible member 14 may be able to speed back up, as indicated by the adjacent lines 102 that are spaced further apart than the lines 102 between the seven-foot position and the nine-foot position. The lines 102 are relatively closer together again between about the twenty-foot and twenty three-foot positions, which correspond to the blockage 106.

When the rate at which the flexible member 14 progresses through the enclosure decreases by a predetermined amount or below a predetermined rate threshold, the controller 20 may generate a flag or bookmark on the visual representation 100 at the location at which the rate decrease occurs. The flag or bookmark may be saved to the memory device 103 along with the visual representation 100.

The flag or bookmark may indicate to an operator or technician that a point of interest exists at the bookmarked location within the enclosure 12. Points of interest may include clogs, bends or turns, the presence of foreign matter or debris and/or other trouble spots within the enclosure 12. Using the display device 101, the operator can cause the controller 20 to retrieve the bookmarked visual representation 100 from the memory device 103 to be displayed on the display device 101 at any convenient time. As will be subsequently described, the operator can then determine the nature of the point of interest and attach notes, comments and/or descriptions of the point of interest to the visual representation 100 and save this information in the memory device 103 for future jobs or for review with colleagues and/or clients, for example.

Figure 9:
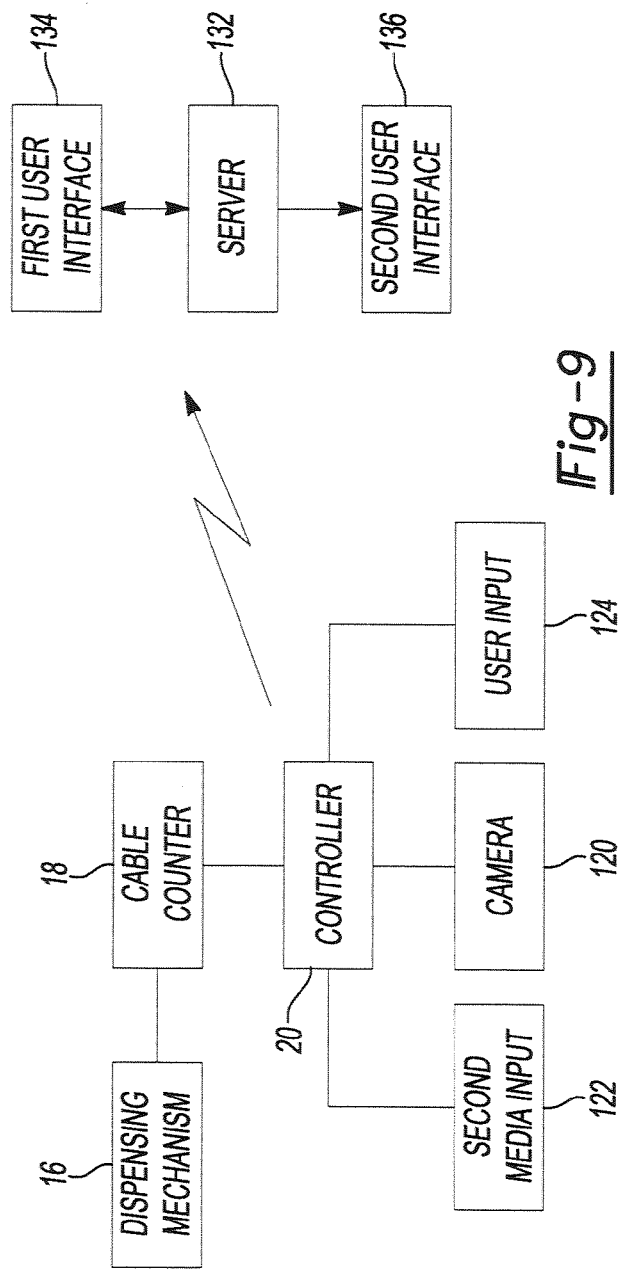
FIG. 9 is a block diagram of yet another embodiment of a probing apparatus according to the principles of the present disclosure.
Figure 10:
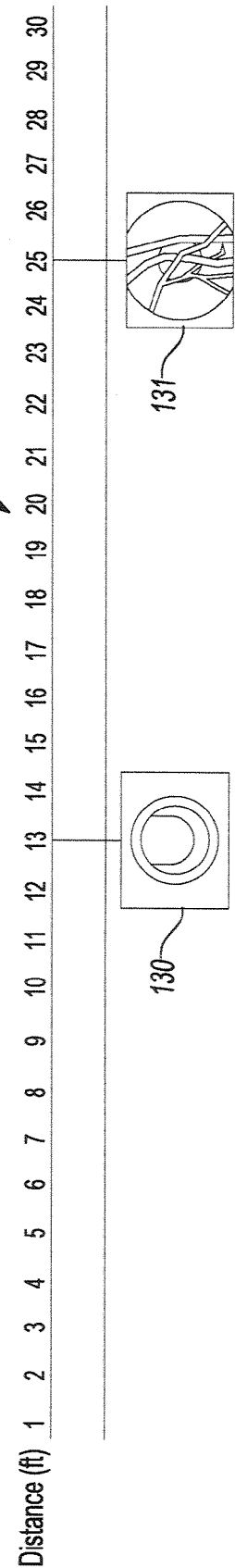
FIG. 10 is another embodiment of a visual representation according to the principles of the present disclosure.

Referring now to FIGS. 9 and 10, the probing apparatus 10 or 10' can further include a camera 120, a second media input device 122 and/or a user input 124. As will be subsequently described, the probing apparatus 10 or 10' may be operable to generate another embodiment of a visual representation 200.

The camera 120 may be any suitably durable still photograph or video camera fixed to the distal end 24 of the flexible member 14. Examples of such cameras are those of the Ridgid® SeeSnake® inspection devices manufactured by Ridge Tool Company. LED lights or any other suitable lights may be disposed on or proximate the camera 120 to illuminate the enclosure 12. The second media input device 122 can be a voice or audio recorder, a phone, a laptop computer, a global positioning system (GPS), or any other information collection device or communication device. The user input 124 can be any suitable switch or push-button known in the art. The user input 124 may be in communication with the controller 20 and can be disposed in any suitable location, preferably where it can be readily accessed by the operator during operation of the probing apparatus 10, 10'.

Video and/or still photographs taken by the camera 120 may be communicated to the controller 20 and may be stored therein. When a point of interest is encountered, the controller 20 may cause the camera 120 to capture a still photograph 130 or a video 131 of the point of interest within the enclosure 12. The photograph 130 or video 131 can be attached to the point of interest on the visual representation 100 or 200 as a thumbnail, for example, as shown in FIG. 10. Since the camera 120 is fixed to flexible member 14, the controller 20 can attach the photograph 130 or video 131 taken of a particular location within the enclosure 12 to the corresponding location on the visual representation 100, 200. The controller 20 may be adapted to analyze metadata stored with the files containing the photograph 130 and/or video 131 to determine the time(s) and location(s) that the one or more photographs 130 and/or videos 131 were taken.

The second media input device 122 may be in communication with the controller 20, and may be operable to provide information to the controller 20 that can be attached to a flag or bookmark on the visual representation. The operator can actuate the user input 124 to manually flag or bookmark a point of interest encountered in the enclosure 12. The operator could review the manually flagged point of interest at a later time and attach information thereto, if desired. The operator could then speak, type or otherwise communicate instructions, comments and/or notes into the second media input device 122. The second media input device 122 could communicate the information to the controller 20, where it can be subsequently attached to the flagged or bookmarked point of interest and stored in the memory device 103.

As shown in FIG. 9, the controller 20 may be in communication with a server 132, which may in turn be in communication with a first user interface 134 and a second user interface 136. The first and second user interfaces 134, 136 can be personal computers, for example, or a network of computers.

The server 132 can be located remotely from a jobsite. The controller 20 may be in wireless communication with the server 132 to remotely upload information collected at a jobsite. Alternatively, the operator may connect the controller 20 to the server 132 via a wired link after completion of a job and upload information collected from the jobsite. Once the information is uploaded to the server 132, the operator may access the information via the first user interface 134, which may be a computer in communication with the server 132 through an internet or network connection. In this manner, the operator may review any points of interest flagged during operation of the probing apparatus 10, 10', as well as add any additional notes, images or other information to the visual representation 100, 200. The visual representation 100, 200 and the information attached thereto can be stored in the server 132 for future reference to aid in diagnosing and servicing future problems that may arise in the enclosure 12.

The server 132 may be adapted to communicate with a second user interface 136, which may be a remotely located computer. For example, if the operator is a contractor or other hired service technician, his or her customer(s) may be interested in viewing the visual representation 100, 200 to verify the thoroughness and completeness of the job. The customer could connect to the server 132 via the second user interface 136 to view the visual representation 100, 200 and the attached information.

As described above, the visual representation 100, 200 and the information attached thereto can be retrieved from the memory device 103 and/or the server 132 at any point in time. This allows an operator to review the visual representation 100, 200 from a past service job at a particular jobsite to prepare for a present or future service job at that jobsite. For example, before a repeat service job at the particular jobsite, the operator can review the visual representation 100, 200 from the past service job at the particular jobsite to determine the location within the enclosure 12 where tree roots have grown in the past. With this information in mind, the operator knows where tree roots within the enclosure 12 are likely to have grown back and may rapidly dispense the flexible member 14 with the cutting tool 59 disposed thereon directly to the location where tree roots had previously grown and remove any new root growth.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An apparatus comprising:
an elongated flexible member adapted to be removably inserted into an enclosure;
a dispensing mechanism operable to selectively dispense and retract said elongated flexible member;
a counter configured to determine an amount of said elongated flexible member dispensed by said dispensing mechanism; and
a controller configured to receive said amount of said elongated flexible member dispensed from the counter, determine a rate at which said elongated flexible member is dispensed, and detect a point of interest in said enclosure based upon a change in the rate at which said elongated flexible member traverses; and
a display in data communication with said controller, wherein said controller causes said rate at which said flexible member is dispensed to be displayed in relation to a visual representation of said enclosure on said display.

2. The apparatus of claim 1 wherein said visual representation includes a scale for said amount of said elongated flexible member dispensed.

3. The apparatus of claim 1 wherein said visual representation includes a series of lines such that spacing between said lines serves as indicia for said rate at which said flexible member is dispensed.

4. The apparatus of claim 1 wherein said controller stores in increments said amount of said elongated flexible member dispensed and said rate at which said elongated flexible member traverses in a memory device associated with the apparatus.

5. The apparatus of claim 1 wherein said controller stores said amount of said elongated flexible member dispensed at said point of interest in a memory device associated with the apparatus.

6. The apparatus of claim 1 further comprises a user input in communication with said controller and configured to capture indicia of a point of interest from an operator.

7. The apparatus of claim 1 further comprises a camera disposed on said elongated flexible member and in data communication with said controller, such that said visual representation includes an image captured by said camera.

8. The apparatus of claim 7 wherein said visual representation provides indicia of where said image was captured in relation to said scale.

9. An apparatus comprising:
a support;
a drum rotatably coupled to said support, said drum including a housing portion defining an opening therethrough;
a cable coiled around said drum and adapted to selectively dispense therefrom through said opening and into an enclosure;
a cable follower rotatable relative to said drum and configured to guide said cable through said opening;
a first sensor fixed relative to a portion of said drum;
a second sensor fixed relative to a portion of said cable follower, said first and second sensors sensing relative movement therebetween and generating a signal indicative of said relative movement; and
a controller adapted to receive said signal, determine an amount of cable dispensed and a rate at which said cable is dispensed based on said signal, and detect a point of interest in said enclosure based upon a change in said rate at which said cable traverses,
wherein said controller is operable to generate a visual representation including indicia of said rate at which said cable is dispensed relative to a segment of said enclosure and indicia of a change in said rate relative to said segment of said enclosure.

10. The apparatus of claim 9 wherein said visual representation includes a scale for said amount of cable dispensed.

11. The apparatus of claim 9 wherein said visual representation includes a series of lines such that spacing between said lines serves as indicia for said rate at which said cable is dispensed.

12. The apparatus of claim 9 wherein said controller stores in predetermined time increments said amount of said cable dispensed and said rate at which said cable traverses in a memory device associated with the apparatus.

13. The apparatus of claim 9 wherein said controller stores said amount of cable dispensed at said point of interest in a memory device associated with the apparatus.

14. The apparatus of claim 9 further comprises a user input in communication with said controller and configured to capture indicia of a point of interest from an operator.

15. The apparatus of claim 9 further comprises a camera disposed on said cable and in data communication with said controller, such that said visual representation includes an image captured by said camera.

16. The apparatus of claim 15 wherein said visual representation provides indicia of where said image was captured in relation to said scale.

17. An apparatus comprising:
a flexible member adapted to be removably fed into an enclosure through an opening therein;
a camera disposed on a distal end of said flexible member and adapted to capture at least one image frame within said enclosure;
a counting device configured to determine a distance that said distal end has been fed into said enclosure; and
a controller in communication with said camera and said counting device, said controller is adapted to generate a visual representation of at least a segment of said enclosure and detect a point of interest in said enclosure based upon a change in a rate at which said flexible member traverses, said visual representation including indicia of distances from said opening in said enclosure over which said distal end has been fed, wherein said at least one image frame is associated with at least one of said indicia of distances and is selectively viewable in said visual representation.

18. The apparatus of claim 17 wherein said visual representation includes a scale for said amount of said flexible member dispensed.

19. The apparatus of claim 17 wherein said visual representation includes a series of lines such that spacing between said lines serves as indicia for said rate at which said flexible member is dispensed.

20. The apparatus of claim 17 wherein said controller stores in predetermined length increments said amount of said elongated flexible member dispensed and said rate at which said elongated flexible member traverses in a memory device associated with the apparatus.

21. The apparatus of claim 17 wherein said controller stores said amount of said flexible member dispensed at said point of interest in a memory device associated with the apparatus.

22. The apparatus of claim 17 further comprises a user input in communication with said controller and configured to capture indicia of a point of interest from an operator.

23. The apparatus of claim 17 further comprises a camera disposed on said flexible member and in data communication with said controller, such that said visual representation includes an image captured by said camera.

24. The apparatus of claim 23 wherein said visual representation provides indicia of where said image was captured in relation to said scale.

\* \* \* \* \*